United States Patent
Piccirilli

(10) Patent No.: US 8,735,615 B2
(45) Date of Patent: May 27, 2014

(54) METHOD FOR EXTRACTING UNSAPONIFIABLES FROM RENEWABLE RAW MATERIALS

(75) Inventor: Antoine Piccirilli, Poiters (FR)

(73) Assignee: Valagro Carbone Renouvelable Poitou-Charentes, Poitiers (FR)

( * ) Notice: Subject to any disclaimer, the term of this patent is extended or adjusted under 35 U.S.C. 154(b) by 278 days.

(21) Appl. No.: 13/503,509

(22) PCT Filed: Oct. 21, 2010

(86) PCT No.: PCT/FR2010/052247
§ 371 (c)(1),
(2), (4) Date: Apr. 23, 2012

(87) PCT Pub. No.: WO2011/048339
PCT Pub. Date: Apr. 28, 2011

(65) Prior Publication Data
US 2012/0209018 A1    Aug. 16, 2012

(30) Foreign Application Priority Data

Oct. 23, 2009 (FR) .................................... 09 57457

(51) Int. Cl.
*C11B 1/10* (2006.01)
*C11B 3/06* (2006.01)

(52) U.S. Cl.
USPC ............... 554/13; 554/206; 554/21; 554/31; 554/8; 554/9; 554/12; 554/18; 554/20; 554/177; 554/169

(58) Field of Classification Search
None
See application file for complete search history.

(56) References Cited

U.S. PATENT DOCUMENTS

| 5,262,163 | A  | * | 11/1993 | Rancurel ...................... 424/769 |
| 6,146,616 | A  |   | 11/2000 | Msika et al. |
| 2004/0018258 | A1 | * | 1/2004 | Piccirilli et al. .............. 424/769 |
| 2010/0266745 | A1 |   | 10/2010 | Hoang et al. |

FOREIGN PATENT DOCUMENTS

FR    2 762 512 A1    10/1998
GB      988 650 A1     4/1965

OTHER PUBLICATIONS

International Search Report, dated Jan. 24, 2011, from corresponding PCT application.

* cited by examiner

*Primary Examiner* — Yate K Cutliff
(74) *Attorney, Agent, or Firm* — Young & Thompson

(57) ABSTRACT

A method for extracting an unsaponifiable fraction from a renewable raw material selected among oilfruits, oleaginous seeds, oleoproteaginous seeds, seed husks, oil-yielding almonds, sprouts, stones and cuticles of fruits, high-fat raw materials from animals, algae, fungus or yeast, includes the following steps: a) dehydrating and packaging the renewable raw material, not resulting in any extraction of the fat; b) reactive crushing of the fatty packaged raw material in the presence of a light alcohol and a catalyst; c) evaporating the light alcohol; d) concentrating the liquid phase such as to obtain a concentrate including the unsaponifiable fraction diluted in fatty acid alkyl esters; e) saponifying the unsaponifiable concentrate; f) extracting the unsaponifiable fraction from the saponified mixture. The use of an unsaponifiable fraction or co-products obtained by implementing the method for preparing a composition such as a cosmetic, drug, food, or food additive or supplement is also described.

12 Claims, 1 Drawing Sheet

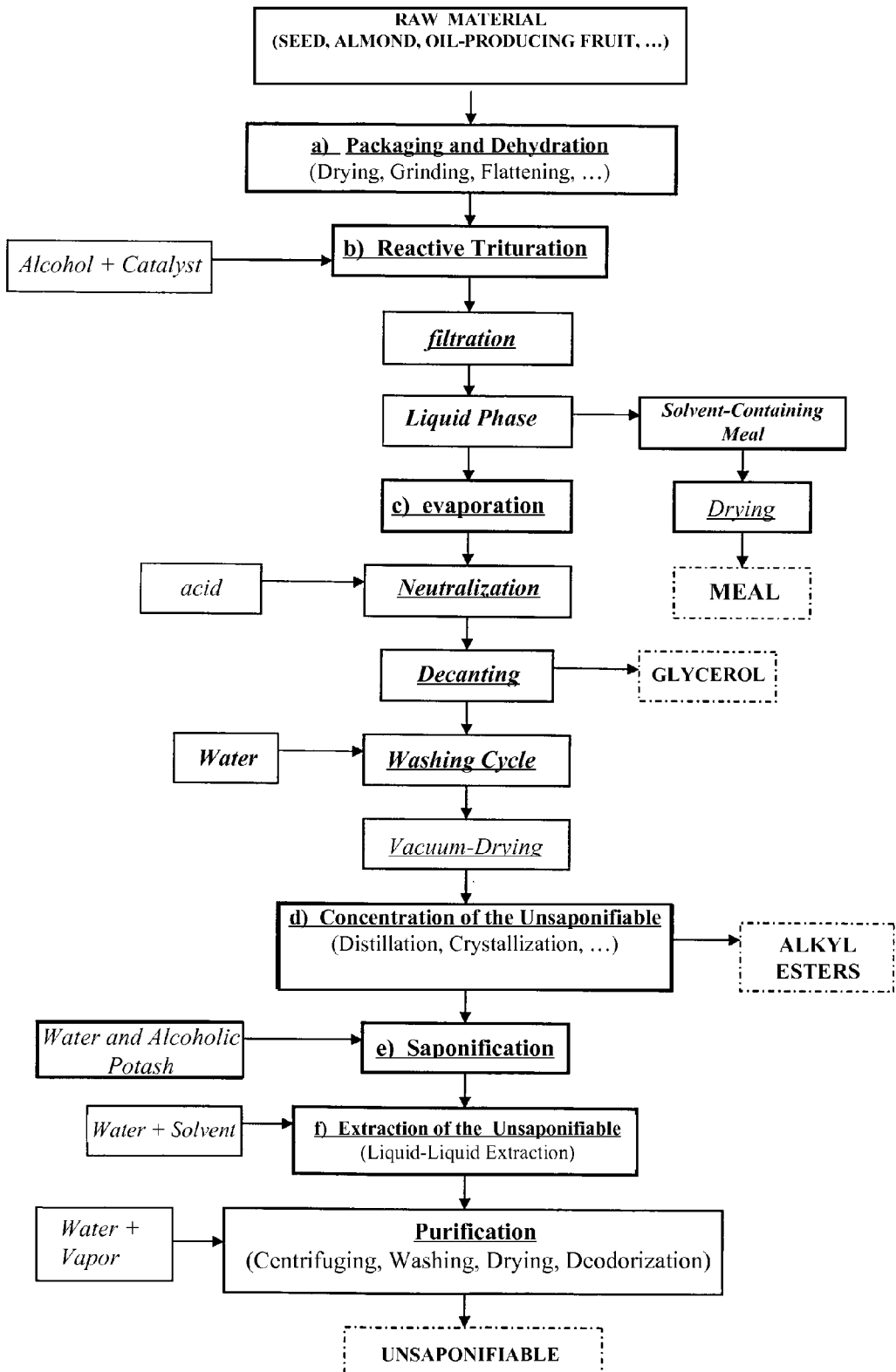

METHOD FOR EXTRACTING UNSAPONIFIABLES FROM RENEWABLE RAW MATERIALS

This invention relates to a process for the extraction of unsaponifiables from a renewable lipidic raw material, in particular an oil-producing fruit, an oleaginous seed, or an animal, algal, fungal or yeast raw material.

By definition, unsaponifiables or minor compounds of a fatty substance are defined as all of the compounds that remain insoluble in water and soluble in an organic solvent after total saponification of said fatty substance, i.e., under the sustained action of an alkaline base.

These unsaponifiables can be, for example, saturated or unsaturated hydrocarbons, sterols, aliphatic and terpenic alcohols, tocopherols and tocotrienols or else carotenoid pigments and xanthophylls.

Currently, as a lipidic raw material, the conventional processes for the extraction of unsaponifiables from a fatty substance generally use vegetable oils and their derivatives and co-products: semi-refined or refined raw vegetable oils, semi-refined or refined unsaponifiable concentrates of vegetable oils that are obtained by molecular distillation of raw vegetable oils, and deodorization outflows.

These processes most often comprise a stage for saponification of the fat followed by a liquid-liquid extraction using an organic solvent.

During the implementation of these extraction methods, the glycerides of the fat are destroyed by soaps. However, these soaps are co-products that—because of their emulsifying properties—are often entrained with glycerin in washing waters that they contaminate with COD (Chemical Oxygen Demand). It is therefore necessary to initiate their acidification in free fatty acids, which is restrictive and only allows an upgrading with very low added value in a soap or detergent factory.

In addition, only the oils and deodorization outflows (soy, canola, sunflower, corn, etc., and mixtures thereof) can be used as raw materials with these known methods. However, there are numerous raw materials of different natures, such as, for example, oil-producing seeds or fruits, containing high-purity unsaponifiables that have advantageous properties.

It is known that these raw materials can be treated by other processes, but the latter do not allow the selective extraction of unsaponifiable fractions. By way of example, it is possible to cite the application FR-2919303 that describes a method for direct preparation of fatty acid ethyl esters by transesterification in the presence of ethanol, alcoholic potash as catalyst, and canola flakes after flattening of seeds, without, however, allowing an extraction of unsaponifiables.

There is therefore a need for a process that makes it possible to extract the unsaponifiables from fatty substances other than oils, whose implementation is economical and also makes it possible to recover co-products of glycerides with higher added value than the free fatty acids.

To respond to this, the invention has as its object a process for extraction of an unsaponifiable fraction of a renewable raw material that is selected from among oil-producing fruits, oleaginous seeds, oleoproteaginous seeds, seed husks, oleaginous almonds, sprouts, pits and cuticles of fruits, and lipid-rich animal, algal, fungal or yeast raw materials, characterized in that it comprises the following stages:

a) Dehydration and packaging of the renewable raw material, not leading to any extraction of fat,
b) Reactive trituration of the packaged lipidic raw material in the presence of a light alcohol and a catalyst,
c) Evaporation of light alcohol,
d) Concentration of the liquid phase so as to obtain a concentrate that comprises the dilute unsaponifiable fraction in fatty acid alkyl esters,
e) Saponification of unsaponifiable concentrate,
f) Extraction of the unsaponifiable fraction of the saponified mixture.

The invention also has as its object the use of unsaponifiables and co-products that are obtained for the preparation of cosmetic compositions, pharmaceutical compositions, and/or food supplements that contain them.

Advantageously, this process makes it possible to obtain unsaponifiables starting from raw materials that were never used directly until then, i.e., without preliminary extraction of the lipids, as well as glyceride co-products with high added values such as fatty acid alkyl esters, and glycerin as well as upgradable meal for animal feed. In addition, the process according to the invention is economical because it does not require the heavy investments of conventional processes. It is also less energy-intensive and requires lower fresh water consumption in comparison to the refining operations of crude oils.

The invention will now be described in detail with regard to the attached FIG. 1 on which is shown a diagram of a particular embodiment of the process for extraction of an unsaponifiable fraction of a renewable raw material.

The object of the invention is therefore a process for the extraction of an unsaponifiable fraction of a lipidic renewable raw material. This raw material is selected from among oil-producing fruits, oleaginous seeds, oleoproteaginous seeds, seed husks, oleaginous almonds, sprouts, pits and cuticles of fruits, and lipid-rich animal, algal, fungal or yeast raw materials.

According to a first embodiment, the raw material is an oil-producing fruit, in particular an oil-producing fruit that is selected from among the olive, shea, palm or avocado. If the oil-producing fruit is an avocado, it can be used fresh or heated up to make the characteristic furanic compounds of the heat-treated avocado appear.

According to a second embodiment, the raw material is a seed, an almond, a sprout, a cuticle or a pit of a plant raw material that is selected from among canola, soy, sunflower, cotton, wheat, corn, rice, grape, walnut, hazelnut, lupine, camelina, flax, safflower, copra, peanut, jatropha, castor oil, neem, hemp, cuphea, lesquerella, inca inchi, perilla, echium, evening primrose, borage, blackcurrant, pine of Korea, cotton, sesame, amaranth, coffee, oats, tomato, marigold, and buriti.

The lipidic raw material can also be an animal raw material, an algae, a mushroom, a yeast or a mold. Among the animal raw materials, the following will be preferred: liver and fish-skin, most particularly those of shark, cod and chimera, as well as the solid wastes from the meat industry.

The process according to the invention comprises a first stage a) for dehydration and packaging of the renewable raw material. The dehydration can be implemented before or after the packaging. By way of example, the oil-producing fruits are preferably dehydrated before being packaged, whereas conversely, the oleaginous seeds are first flattened or ground before dehydration.

Dehydration is defined as the total or partial elimination of water from the raw material. Very preferably, the lipidic raw material is dehydrated in such a way that the residual moisture is less than or equal to 3% by weight of dry material.

Dehydration can be carried out by, for example, drying on a fluidized bed, drying under a hot air stream on a fixed bed, or else by azeotropic distillation, or any other means that is known to one skilled in the art.

The raw material is packaged by implementing a packaging stage that does not lead to any extraction of fat.

Preferably, the renewable raw material is packaged by flattening, flaking, blowing or grinding in powder form. By way of example, the raw material can be toasted or flaked, or else packaged by freeze-drying, pervaporation, spraying, mechanical grinding, cryogrinding, flash-expansion (rapid drying by vacuum and rapid decompression), flattening on a flattener with rollers, or by blowing by introduction of hot air or superheated vapor.

Once dehydrated and packaged, the raw material undergoes a stage b) for reactive trituration of the material in the presence of a light alcohol and a catalyst.

Reactive trituration is defined as any operation whose purpose is to transform the saponifiable lipids into fatty acid alkyl esters and into glycerol, preferably in the presence of one or more reactive elements. In this case, trituration is carried out in the presence of a light alcohol and a catalyst.

The presence of light alcohol makes it possible to transform the glycerides into alkyl esters.

Preferably, the light alcohol is selected from among methanol, ethanol, propanol, isopropanol, butanol, pentanol, hexanol, ethyl-2-hexanol, and isomers thereof.

Likewise, the catalyst is preferably a basic catalyst that is selected from among alcoholic soda, solid soda, alcoholic potash, solid potash, sodium or potassium methylate, sodium or potassium ethylate, sodium and potassium propylate, sodium and potassium isopropylate, amines and polyamines, or an acid catalyst that is selected from among sulfuric acid, nitric acid, paratoluenesulfonic acid, hydrochloric acid and Lewis acids.

This stage b) can be carried out in particular in a batch reactor with a stirred bed or in a continuous reactor with a conveyor belt of the continuous extractor type.

The reactive trituration stage makes it possible to recover, on the one hand, a liquid phase, and, on the other hand, a solvent-containing meal.

The solvent-containing meal can be dried, and then it can be used directly in particular in animal feed.

The liquid phase next undergoes an evaporation stage of the light alcohol. The light alcohol is actually to be evaporated so as to recover the lipids.

After evaporation, the lipidic product that is obtained can undergo a neutralization stage, preferably by an acid, and then a decanting stage that makes it possible to recover glycerol, on the one hand, and a lipidic phase.

The lipidic phase is next to be concentrated in such a way as to obtain, on the one hand, a concentrate that comprises the dilute unsaponifiable fraction in fatty acid alkyl esters, and, on the other hand, high-purity alkyl esters, i.e., clear and colorless esters that have an ester content that is greater than 98% and an unsaponifiable content that is less than 0.1%. This fraction of high-purity esters having an ester content of greater than 98% can be used directly in particular in cosmetics or in pharmaceuticals.

The concentration stage in particular can be implemented by distillation or by crystallization. Distillation is defined as any technique that is known by one skilled in the art, in particular molecular distillation, distillation at atmospheric pressure or under vacuum, multi-staged in series, azeotropic distillation, hydrodistillation, and deodorization in the presence of vapor or an inert gas (nitrogen, carbon dioxide).

The distillation makes it possible to obtain a light fraction that is called a distillate that comprises high-purity alkyl esters and a heavy fraction that is called a residue that comprises the dilute unsaponifiable fraction in fatty acid alkyl esters.

This stage can be implemented in, for example, a centrifuge molecular distiller or a wiped film distiller, in a wiped film evaporator or a falling film evaporator, or else in a thin-layer deodorizer that operates under vacuum with or without injection of vapor, nitrogen or carbon dioxide.

The concentrate (the heavy fraction in the case of a distillation) next undergoes a saponification, i.e., a chemical reaction that transforms an ester into a water-soluble carboxylate ion and an alcohol.

Next, the unsaponifiable fraction is extracted from the saponified mixture. Preferably, this stage is implemented by liquid-liquid extraction using an organic solvent.

The organic solvent in particular can be an organic synthesis solvent that is selected from among alkanes, aromatic compounds, haloalkanes, ethers and ketones, or an organic solvent of natural origin that is selected from among terpenes, such as limonene, alpha-pinene, beta-pinene, myrcene, linalol, citronellol, geraniol, menthol, citral, citronellal, or oxidized organic derivatives, in particular ethers, aldehydes, alcohols and esters, such as, for example, furfural and furfurol.

The extraction can be done on an extraction column with co-current or counter-current or else using a series of decanter-mixers.

Once extracted, the unsaponifiable fraction is preferably purified, in particular by desolventation, washing, drying and/or vacuum deodorization. The purification stage can be carried out in particular by the implementation of the following sub-stages:

Centrifuging of the solvent phase in such a way as to extract residual soaps,

Washing the solvent phase with water,

Vacuum evaporation of the solvent by vacuum distillation, by hydrodistillation or by azeotropic distillation, Vacuum deodorization of the unsaponifiable fraction so as to extract from it—under deodorization conditions—any remaining contaminant, in particular the extraction solvent, pesticides, or polycyclic aromatic hydrocarbons.

The process according to the invention makes it possible to obtain pure unsaponifiables of an origin that is different from the one that is conventionally proposed.

In a non-exhaustive manner, the minor compounds or unsaponifiables that are obtained according to the invention are sterols, tocopherols, tocotrienols, squalene, polycosanols, triterpenic alcohols, fatty polyols and furanic compounds of the avocado, sesamine and sesamolin, beta-carotene, lycopene, lutein, asthaxanthin, the Q10 co-enzyme, calciferol, cholecalciferol, alkyl glycerols, limonoids, and azadirachtin.

One particular example of the process according to the invention is illustrated in FIG. 1.

The raw material is first dehydrated and packaged or packaged and dehydrated (stage a).

Next, it undergoes reactive trituration in the presence of a light alcohol and a catalyst (stage b). The product that is obtained is filtered in such a way as to recover, on the one hand, a solvent-containing meal, and, on the other hand, a lipidic liquid phase.

The solvent-containing meal is dried.

The lipidic liquid phase undergoes a stage of evaporation of the light alcohol (stage c), and then a neutralization using an acid and a decanting that makes it possible to recover glycerol. The remaining lipidic phase is washed with water and vacuum-dried.

The following stage is a stage for concentration of the unsaponifiable (stage d) in such a way as to recover high-purity alkyl esters, on the one hand, and a concentrate, on the other hand.

Next, the concentrate is saponified using an alcoholic potash (stage e), and then an extraction of the unsaponifiable fraction is carried out (stage f) with water and another solvent.

The unsaponifiable fraction is finally purified, by centrifuging, washing, drying and deodorization.

The invention offers numerous advantages relative to the existing conventional processes that are used for the extraction starting from oils or deodorization outflows. In terms of investment, first of all, the process according to the invention makes it possible to eliminate mechanical trituration tools such as a screw press or a hexane extractor, and refining tools (degumming, neutralization). In addition, contrary to the mechanical trituration or hexane evaporation, and refining, the reactive trituration according to the invention does not produce high energy consumption. It no longer brings about consumption of fresh water unlike crude oil refining operations.

In addition, the invention is very advantageous in terms of co-upgrading because the implementation of the process leads to co-products such as:
  Directly upgradable, high-purity alkyl esters in cosmetics or pharmaceuticals,
  Glycerin that finds applications in cosmetics, pharmaceuticals, hygiene products, anti-gel fluids, etc., and
  Directly upgradable meal for animal feed.

This invention also has as its object the use of an unsaponifiable fraction or co-products that are obtained for the implementation of the process for the preparation of a cosmetic composition, a medicinal composition, a food composition or food supplements or additives. Advantageously, this unsaponifiable fraction and the co-products that are obtained according to the invention do not contain toxic solvent residues and have much better regulatory safety and acceptability (linked to the absence of toxic residual solvent) than the products that are obtained by the implementation of conventional processes. These particular characteristics make possible a more suitable use as a cosmetic composition, medicinal composition, food composition, or food supplements or additives.

The invention will now be illustrated through various examples.

EXAMPLE 1

Extraction of Minor Compounds from a Sesame Seed

For this first test, the raw material that is used is a sesame seed that has the following characteristics:
  Water content: 8% by weight of dry material,
  Fat content: 45.0% by weight of dry material.

After extraction using a Soxhlet-type device according to the NF ISO 659 method, the analysis of oil extracted according to the NFT 60-205-1 method reveals an unsaponifiable fraction content of 0.8% by weight of fat. The thin-layer chromatography analysis of the unsaponifiable implemented in the presence of a hexane/ether eluant mixture (2/1 by volume) reveals the presence—as majority components—of sesamine, sesamolin, and phytosterols. Likewise, the acidity of the oil of the seed determined by the NFT 60-204 method is 5.0 mg of KOH/g.

In a first stage, 1,000 g of unhusked seeds are dried for study at 80° C. for 24 hours. The final moisture of the seed is 0.8% by weight of dry material. The dried seeds are then flattened using a cylinder flattener so as to obtain 878 g of flakes.

In a 2-liter glass reactor that is equipped with a bulb condenser, a double jacket, and a mechanical stirring mechanism, 678 g of flakes is then brought into the presence of 1,756 g of anhydrous ethanol and 8.4 g of soda scales that were previously dissolved in 200 g of anhydrous ethanol. While being stirred, the mixture is brought to 55° C. for 30 minutes. Next, the mixture is filtered on a Büchner filter, and the cake is washed with 3 times 100 ml of ethanol.

Next, the filtrate is neutralized at 50° C. by adding 100 ml of an alcoholic sulfuric acid solution that contains 3 g of $H_2SO_4$. The ethanol is then distilled under vacuum (300 mbar) with the rotary evaporator at a temperature of 30° C. for 30 minutes.

The mixture that is obtained is then in two phases since the decanting of the glycerin-containing phase is observed. The glycerin is then extracted by centrifuging at 3,500 rpm. Finally, the ester phase that is obtained is washed by adding demineralized water (6 successive washing cycles, or, for each washing cycle, 6% water by weight of the ester phase), and then vacuum-dried in the rotary evaporator, at 90° C. (20 mbar) for 30 minutes. 320 g of ethyl esters is then obtained.

The ester phase is then sent into a molecular distiller with KDL4-type wiped film. The temperature is set at 140° C., and the vacuum is set at 0.008 mbar. The distillate yield is 96.2%. The heavy phase that is loaded with unsaponifiables and ethyl esters has an unsaponifiable content of 20.5% by weight of fat.

In a 100 ml flask that is equipped with a condenser, the heavy phase (11.5 g) is placed in the presence of 48 ml of 3.7 M alcoholic potash and several glass balls. The mixture is then brought to reflux (95° C.) for 4 hours. After cooling, the medium is diluted with 75 ml of demineralized water. The hydroalcoholic mixture that is obtained is then extracted by limonene (extraction solvent) that is provided by the Interchimie company.

The extraction is done with an ampoule that is to be decanted (500 ml). The saponified medium is introduced into the ampoule that is to be decanted with 100 ml of limonene that is obtained from the operation for rinsing the saponification flask. After decanting, the organic phase is separated from the aqueous phase, the latter being taken up again by 100 ml of limonene. The aqueous phase thus undergoes 4 successive extractions in the presence each time of 100 ml of limonene.

The organic phases are then consolidated and then washed by adding demineralized water until neutrality is reached (monitoring with pH paper). Each washing cycle is carried out by adding 100 ml of water.

The limonene solvent is then eliminated by vacuum distillation: at 140° C. under 20 mbar. The distillation residue that is obtained, consisting of unsaponifiable compounds that are initially present in the heavy phase that is obtained by molecular distillation, is then weighed precisely and then analyzed by thin layer chromatography (TLC). 2.1 g of unsaponifiable compounds is obtained.

The overall yield of the unsaponifiable extraction process is 63%.

The table below consolidates the results of thin layer chromatography (TLC) analysis of the unsaponifiable fractions of the sesame oil that is present in the seed (obtained by the NFT 60-205-1 method) and the unsaponifiable that is extracted during the reactive trituration process.

|  | Unsaponifiable Sesame Fractions | |
| --- | --- | --- |
| Analysis and Observations | NFT 60-205-1 Method | Process for Reactive Trituration of Seeds |
| TLC Analysis | | |
| Intensity of Sterol Spots | ++++ | ++++ |
| Intensity of Sesamine and Sesamolin Spots | ++++ | ++++ |
| Intensity of Tocopherol Spots | ++ | ++ |

The results of Table 1 indicate that the process for reactive trituration of seeds makes it possible to obtain—with an appreciable yield—an unsaponifiable fraction that has a composition that is very close, and even identical, to that of the unsaponifiable that is present in the lipids of the seed (NFT 60-205-1 method).

Likewise, the ethyl esters that are obtained in the molecular distillation distillate are clear and have a colorless appearance and exhibit a final acidity of 0.5 mg of KOH/g as well as an ethyl ester purity of 99.3%. Because of their quality and their appearance, these esters constitute an upgradable co-product of the process that can be designed for cosmetic and pharmaceutical applications.

EXAMPLE 2

Extraction of Minor Compounds from an Avocado

For this first test, the raw material that is used is 10 kg of fresh avocado of the Haas variety that has the following characteristics:

Water content: 91.7%
Fat content of the dry material: 38.3% by weight of dry material
Acidity of the fat: 2.1 mg of KOH/g, and
Unsaponifiable content of the fat: 4.2% by weight of fat.

In a first stage, the fresh avocados are cut into slices (pit included). Next, the slices are dried under air in the ventilated oven at 70° C. for 36 hours. The residual moisture of the sliced avocado is 6.3% by weight of fat. The slices are then ground in a mixer for the purpose of obtaining a powder with a grain size of between 0.2 and 0.4 mm. This powder is then freeze-dried until a moisture that is less than 3% by weight of fat is reached. Thus, 758 g of dry avocado powder (residual moisture of 0.9% by weight of fat) is obtained.

In a second stage, this 758 g of avocado in powder form is placed in a 5-liter glass reactor, equipped with a bulb condenser, a double jacket, and a mechanical stirring mechanism, in the presence of 2,000 g of anhydrous ethanol and 9.9 g of soda in scales previously dissolved in 240 g of anhydrous ethanol. While being stirred, the mixture is brought to 55° C. for 45 minutes. Next, the mixture is filtered on a Büchner filter, and the cake is washed with 5 times 120 ml of ethanol.

Next, the filtrate is neutralized at 50° C. by adding 100 ml of an alcoholic sulfuric acid solution that contains 3.5 g of $H_2SO_4$. The ethanol is then vacuum-distilled (500 mbar) in the rotary evaporator and at a temperature of 70° C.

The mixture that is obtained is then in two phases since the decanting of the glycerin-containing phase is observed. The glycerin is then extracted by centrifuging at 3,500 rpm. The ester phase that is obtained is finally washed by adding demineralized water (6 successive washing cycles, or, for each washing cycle, 6% of water by weight of the ester phase), and then vacuum-dried in the rotary evaporator at 90° C. (20 mbar) for 90 minutes. Then, 259 g of a fat phase (ethyl esters) is obtained. A determination of the unsaponifiable content of the ester phase is then initiated according to the NFT 60-205-1 method in which the hexane has been replaced by 1,2 dichloroethane. Also, a TLC analysis of the unsaponifiable is carried out, demonstrating the characteristic compounds of the avocado unsaponifiable of moderately dried fruits: keto-hydroxyl-containing compounds, furanic lipids, fatty polyols, and sterols.

The ester phase is then sent into a molecular distiller with KDL4-type wiped film. The temperature is set at 140° C., and the vacuum is set at 0.008 mbar. The distillate yield is 88.3%. The heavy phase, loaded with unsaponifiables and ethyl esters, has an unsaponifiable content of 35.2%/MG.

In a 100 ml flask that is equipped with a condenser, the heavy phase is placed in the presence of 150 ml of 3.7 M alcoholic potash and several glass balls. The mixture is then brought to reflux (95° C.) for 4 hours. After cooling, the medium is diluted with 150 ml of demineralized water. The hydroalcoholic mixture that is obtained is then extracted by limonene (extraction solvent) that is provided by the Interchimie company.

The extraction is carried out several times with the ampoule that is to be decanted. The saponified medium is introduced into the ampoule that is to be decanted with 100 ml of limonene that is obtained from the operation for rinsing the saponification flask. After decanting, the organic phase is separated from the aqueous phase, with the latter being taken up again by 100 ml of limonene. The aqueous phase thus undergoes 4 successive extractions in the presence each time of 100 ml of solvent.

The organic phases are then consolidated and then washed by adding demineralized water until neutrality is reached (monitoring with pH paper). Each washing cycle is carried out by adding 100 ml of water.

The limonene solvent is then eliminated by vacuum distillation: at 140° C. under 20 mbar. The distillation residue that is obtained, consisting of the unsaponifiable compounds that are initially present in the heavy phase that is obtained by molecular distillation, is then weighed precisely, and then analyzed by thin layer chromatography (TLC). 8.7 g of unsaponifiable compounds is obtained.

The overall yield of the unsaponifiable extraction process is 72%.

The following table consolidates the TLC analysis results of the unsaponifiable fractions of the fatty phase before extraction (analysis of ethyl esters according to the NFT 60-205-1 method that is modified by replacing hexane by 1,2 dichloroethane) and the unsaponifiable that is extracted during the reactive trituration process.

|  | Unsaponifiable Avocado Fractions | |
| --- | --- | --- |
| Analysis and Observations | NFT 60-205-1 (1) Method | Process for Reactive Trituration of the Dehydrated Avocado |
| TLC Analysis | | |
| Intensity of Sterol Spots | + | + |
| Intensity of Furanic Lipid Spots | ++ | ++ |
| Intensity of Keto-Hydroxyl-Containing Compound Spots | Traces | Non-Traces |
| Unidentified Compounds | ++ | ++ |
| Intensity of Polyhydroxyl-Containing Fatty Alcohol Spots | +++ | +++ |

(1) Method that is modified by replacing hexane with 1,2 dichloroethane

The results of the table above indicate that the reactive trituration process that is implemented on the dried avocado makes it possible to obtain—with an appreciable yield (72%)—an unsaponifiable fraction that has a composition that is very close and even identical to the one of the avocado unsaponifiable that is obtained from dried fruits.

Likewise, the avocado ethyl esters that are obtained in the molecular distillation distillate have a colorless appearance and have a final acidity of 0.3 mg of KOH/g as well as an ethyl ester content of 99.6%. Because of their quality and their appearance, these esters constitute an upgradable co-product of the process that can be designed for cosmetic and pharmaceutical applications.

The invention claimed is:

1. Process for extraction of an unsaponifiable fraction of a renewable raw material that is selected from among oil-producing fruits, oleaginous seeds, oleoproteaginous seeds, seed husks, oleaginous almonds, sprouts, pits and cuticles of fruits, and lipid-rich animal, algal, fungal or yeast raw materials, characterized in that it comprises the following stages:
    a) Dehydration and packaging of the renewable raw material, not leading to any extraction of fat,
    b) Reactive trituration of the packaged lipidic raw material in the presence of a light alcohol and a catalyst, in such a way as to recover, on the one hand, a liquid phase, and, on the other hand, a solvent-containing meal,
    c) Evaporation of light alcohol from the liquid phase,
    d) Concentration of the liquid phase so as to obtain a concentrate that comprises the dilute unsaponifiable fraction in fatty acid alkyl esters,
    e) Saponification of unsaponifiable concentrate,
    f) Extraction of the unsaponifiable fraction from the saponified mixture.

2. Process for extraction of an unsaponifiable fraction according to claim 1, wherein the renewable raw material is an oil-producing fruit that is selected from among olive, shea, palm or avocado that is fresh or heated up.

3. Process for extraction of an unsaponifiable fraction according to claim 1, wherein the renewable raw material is a seed, an almond, a sprout, a cuticle or a pit of a plant raw material that is selected from among canola, soy, sunflower, cotton, wheat, corn, rice, grape, walnut, hazelnut, lupine, camelina, flax, safflower, copra, peanut, Jatropha, castor oil, neem, hemp, cuphea, lesquerella, inca inchi, perilla, echium, evening primrose, borage, blackcurrant, pine of Korea, cotton, sesame, amaranth, coffee, oats, tomato, marigold, and buriti.

4. Process for extraction of an unsaponifiable fraction according to claim 1, wherein the renewable raw material is liver or fish-skin, or solid waste from the meat industry.

5. Process for extraction of an unsaponifiable fraction according to claim 1, wherein the dehydration is carried out in such a way as to reach a residual moisture that is less than or equal to 3% by weight of the dry material.

6. Process for extraction of an unsaponifiable fraction according to claim 1, wherein the packaging of the raw material is done by flattening, flaking, blowing, flash-expansion and/or grinding.

7. Process for extraction of an unsaponifiable fraction according to claim 1, wherein the light alcohol is selected from among methanol, ethanol, propanol, isopropanol, butanol, pentanol, hexanol, ethyl-2-hexanol and isomers thereof.

8. Process for extraction of an unsaponifiable fraction according to claim 1, wherein the catalyst is a basic catalyst that is selected from among soda, alcoholic soda, solid soda, potash, alcoholic potash, solid potash, sodium or potassium methylate, sodium or potassium ethylate, sodium and potassium propylate, sodium and potassium isopropylate, amines and polyamines, or an acid catalyst that is selected from among sulfuric acid, nitric acid, paratoluenesulfonic acid, hydrochloric acid and Lewis acids.

9. Process for extraction of an unsaponifiable fraction according to claim 1, wherein the concentration stage is carried out by distillation or by crystallization.

10. Process for extraction of an unsaponifiable fraction according to claim 1, wherein the extraction stage is carried out by liquid-liquid extraction using an organic solvent.

11. Process for extraction of an unsaponifiable fraction according to claim 10, wherein the organic solvent is an organic synthesis solvent that is selected from among alkanes, aromatic compounds, halo-alkanes, ethers and ketones, or an organic solvent of natural origin that is selected from among terpenes and oxidized organic derivatives.

12. Process for extraction of an unsaponifiable fraction according to claim 1, wherein it comprises an additional purification stage that consists of the series of the following sub-stages:
    Centrifuging of the solvent phase in such a way as to extract residual soaps,
    Washing the counter-current solvent phase with water,
    Vacuum evaporation of the solvent by vacuum distillation, by hydrodistillation, or by azeotropic distillation,
    Vacuum deodorization of the unsaponifiable fraction so as to extract from it any remaining volatile contaminant.

* * * * *